United States Patent
Call

[11] Patent Number: 5,928,150
[45] Date of Patent: Jul. 27, 1999

[54] SYSTEM FOR LOCATING AND DETECTING A SOURCE OF PHOTON EMISSIONS

[75] Inventor: John D. Call, Columbus, Ohio

[73] Assignee: Neoprobe Corporation, Dublin, Ohio

[21] Appl. No.: 08/944,078

[22] Filed: Oct. 4, 1997

[51] Int. Cl.[6] .................................................... A61B 6/00
[52] U.S. Cl. ................ 600/436; 250/336.1; 250/370.01
[58] Field of Search .................... 600/431, 436, 600/407; 250/336.1, 363.01, 370.01, 370.07, 370.13

[56] References Cited

U.S. PATENT DOCUMENTS

| | | | |
|---|---|---|---|
| 4,782,840 | 11/1988 | Martin, Jr. et al. | 128/654 |
| 4,801,803 | 1/1989 | Denen et al. | 250/336 |
| 5,246,005 | 9/1993 | Carroll et al. | 128/654 |
| 5,383,456 | 1/1995 | Arnold et al. | 128/653 |
| 5,441,050 | 8/1995 | Thurston et al. | 128/659 |

OTHER PUBLICATIONS

Sugarbaker, E.V., Patterns of Metastasis in Human Malignancies, 1981, pp. 236–273.

Staging of Carcinoma of the Breast Using a Hand–Held Gamma Detecting Probe and Monoclonal Antibody B72,3, Nieroda, 1989, pp. 35–40.

Morton et al, Technical Details of Intraoperative Lymphatic Mapping For Early Stage Melanoma, 1992, 392–399.

Uren et. al, Lymphoscintigraphy in High–Risk Melanoma of the Trunk: Predicting Draining Node GRPS, Defining Lymphatic Channels and Locating the Node, 1993, pp. 1435–1440.

Guiliano, Lymphatic Mapping and Sentinel Lymphadenectomy for Breast Cancer, 1994, pp. 391–401.

*Primary Examiner*—Ruth S. Smith
*Attorney, Agent, or Firm*—Mueller and Smith, LPA

[57] ABSTRACT

System for detecting emissions from a radiopharmaceutical injected within a lymph duct wherein a hand-held probe is utilized. When employed to locate sentinel lymph nodes, supplementary features are provided including a function for treating validated photon event pulses to determine count rate level signals. A function for count rate based ranging as well as an adjustable thresholding feature are also present. A post-threshold amplification circuit develops full-scale aural and visual outputs.

21 Claims, 11 Drawing Sheets

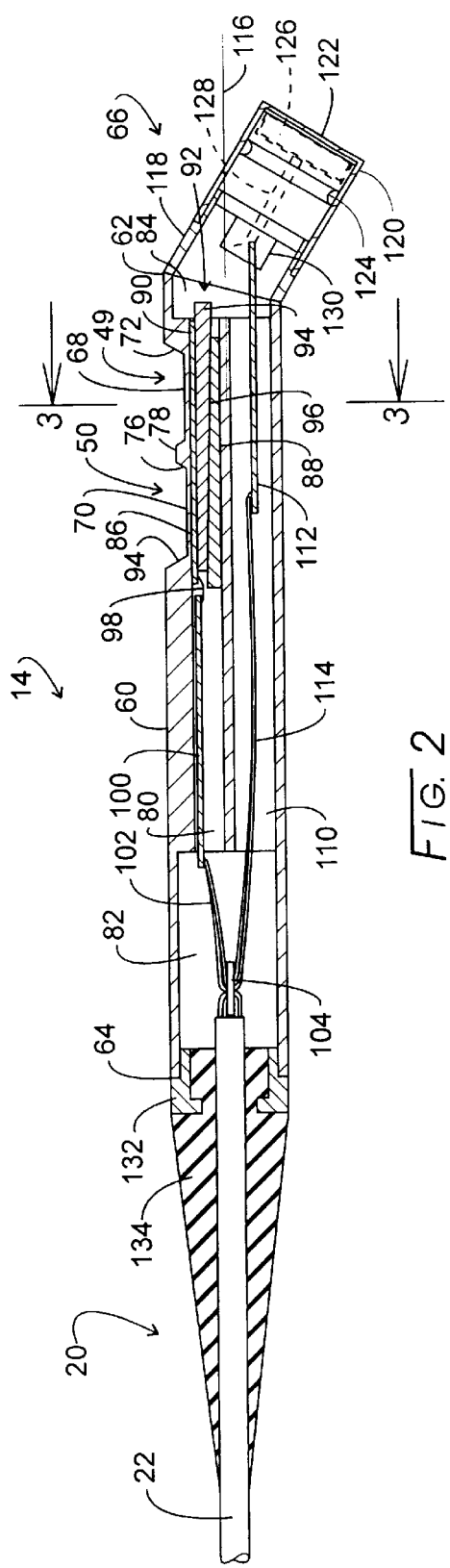
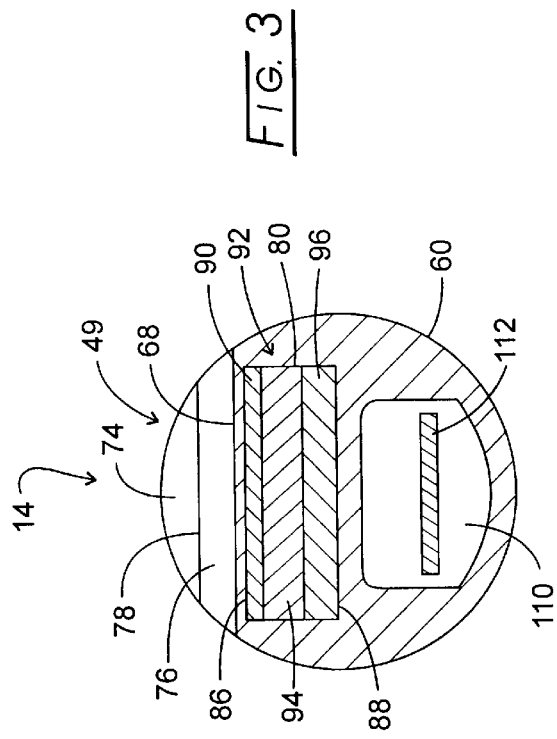
FIG. 2
FIG. 3

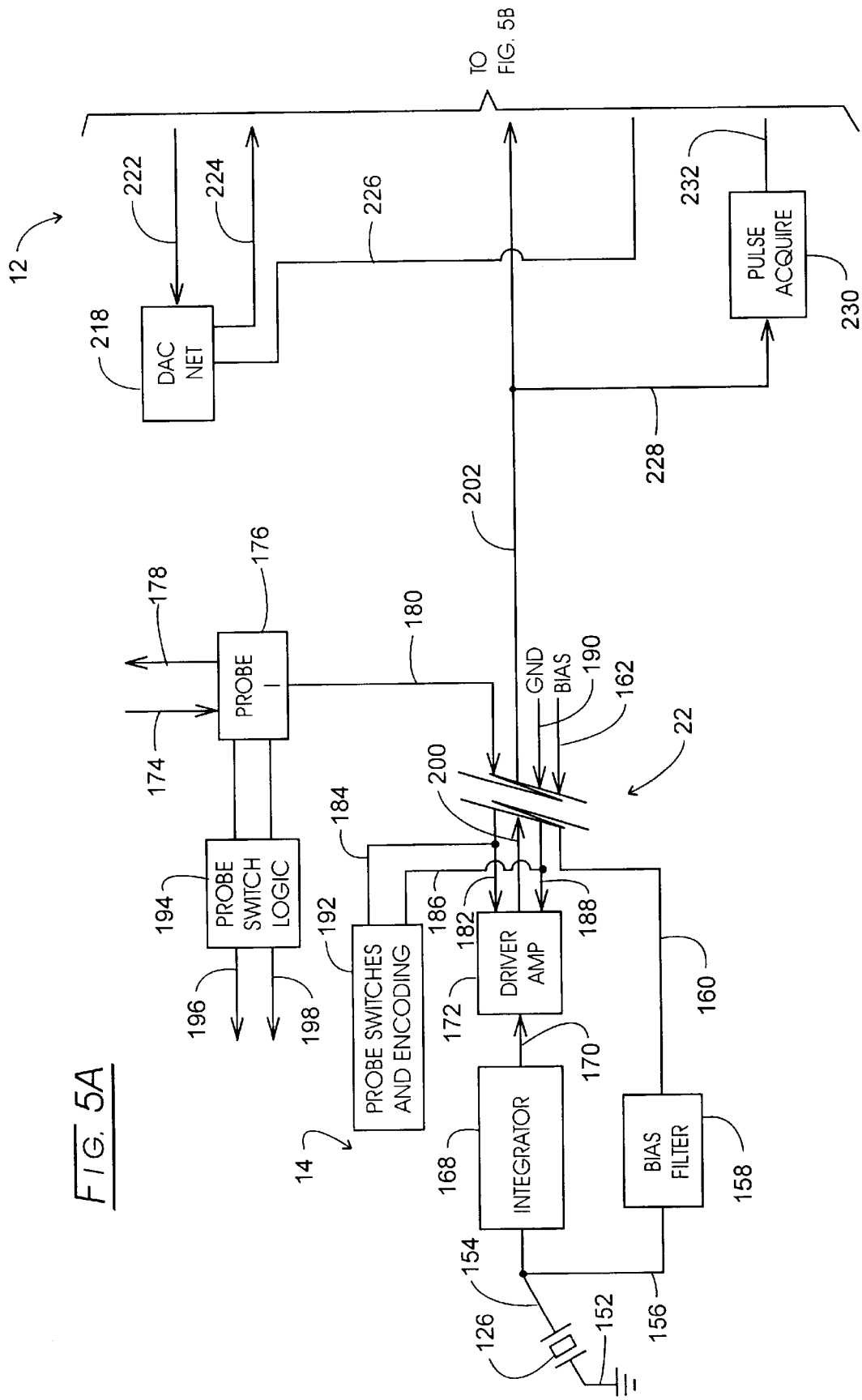

SYSTEM FOR LOCATING AND DETECTING A SOURCE OF PHOTON EMISSIONS

BACKGROUND OF THE INVENTION

An evaluation of the presence or absence of tumor metastasis or invasion has been a major determinant for the achievement of an effective treatment for cancer patients. Studies have determined that about 30% of patients with essentially newly-diagnosed tumor will exhibit clinically detectable metastasis. Of the remaining 70% of such patients who are deemed "clinically free" of metastasis, about one-half are curable by local tumor therapy alone. See Sugarbaker, E. V., "Patterns of Metastasis in Human Malignancies," *Cancer Biol. Rev.* 1981 2:235. The remaining patients will have clinically occult (undetected) micrometastasis that ultimately become manifest.

The involvement of the lymph system in tumor metastasis has been the subject of extensive investigation and is well established. Lymphatic systems are present as widely dispersed tissues, fluids, and cells concerned in a variety of interrelated functions of the mammalian body including the circulation and modification of tissue fluid formed in the capillary beds, and the removal by mononuclear phagocytes of cell debris and foreign matter. The lymphatic system is importantly involved in participation with the blood vascular system in developing the immune response of the lymphocytes and other cells. Lymph flows within the system as a consequence of a variety of perceived mechanisms of organ and tissue dynamics. For certain cancers, metastasis occurring in consequence of lymph drainage will result in initial location or positioning of neoplastic cells at certain lymph nodes typically deemed "regional nodes" within a pertinent lymph drainage basin. Some cancers, for example, melanomas, have been observed to exhibit variability in lymphatic drainage patterns emanating from different portions of the body. Other cancers, such as those encountered in the breast will evidence somewhat more predictable nodal involvement In designing forms of cancer disease management, therefore, efforts are directed to the identification of affected lymph nodes.

For cancers such as breast cancer, the sites of lymph node involvement are commonly encountered at axillary, internal mammary, and supraclavicular lymph node regions. Of these, the axillary lymph node region is the principal site of regional metastasis from carcinoma of the breast, and approximately 40% of patients have evidence of spread to the axillary nodes. In early approaches to the disease, these axillary nodes were removed as a form of therapy. Presently, however, their positive involvement, or lack thereof, has become the subject of diagnostics as opposed to therapy. In this regard, the combination of the presence and extent of metastasis to the axilla represents the single most important prognostic factor for the management of patients with breast cancer. See generally "Cancer, Principles and Practice of Oncology", vol. 1, 4th ed. DeVita, Jr., et al., chapter 40, Harris, et al., J. P. Lippincott Co., Philadephia, Pa. (1993).

The axilla is a triangular region bounded by the axillary vein superiorly, the *latissimus dorsi* laterally, and the *serratus* anterior medially. With more current diagnostic procedures, essentially all axillary nodes at the axilla assumed to represent the drainage basin are removed during surgery for analysis. In general, somewhere between 10 and 30 nodes will be removed in the course of dissection with, of course, the attendant risks. In this regard, these nodes are generally surrounded by investment or fatty tissue and visualization of them necessarily is limited. Such dissection will pose risks of cutting the long thoracic nerve, the thoracic-dorsal nerve, the nerve to the *pectoralis major* or the axillary vein. Morbidity may occur in some cases due to regional node removal and patients are known to frequently discuss a numbing of the arm region following the procedure.

While this form of somewhat radical axillary lymph node dissection has been the conventional approach to determining nodal metastatic involvement, more recent data suggests that less radical axiliary node evaluation procedures may generate equivalent information for staging and patient management, but with far more limited dissection and resultant trauma, as discussed below.

Patient management for staging purposes for the case of cutaneous melanoma is highly predicated upon determinations of lymph involvement. A number of factors are involved in the prognosis of the disease, including, inter alia, location, tumor thickness, level of invasion, growth patterns, and of particular importance the identification of regional node metastatic involvement. Generally, surgical excision of metastatic nodes within the drainage basin of a lesion has been considered the only effective treatment for cure or disease control. Some investigators have preferred to excise only clinically demonstrable metastatic nodes associated with the lesion, while others have chosen to excise the nodes even where they may appear normal because of the risk of the presence of occult (clinically undetectable) metastasis. A substantial dialog has been carried on by investigators as to whether or not elective lymph node dissection or lymphadenectomy is an appropriate therapy. Elective lymphodenectomy has the major advantage of treating a nodal metastasis at a relatively early stage in its natural history when the tumor burden is low. On the other hand, such an approach may subject patients to surgery which would otherwise have been unnecessary. In particular, where patients exhibit a clinical Stage I level of the disease, there will be no nodal metastasis present and no benefit then can be realized from regional lymphadenectomy.

Relatively recently, Morton, et al., undertook an investigation of a procedure designed to identify that lymph node nearest the site of a melanoma and within the pertinent lymph drainage basin. Such a node, being on the most direct drainage pathway will present the most likely site of early metastasis and is referred to as the "sentinel node". Thus, by carrying out only a limited dissection specific to this node and performing pathologic analysis of it, staging can be achieved without at least initial resort to more radical lymphadenectomy. With the approach, once the drainage basin from a lesion is identified, for example, by lymphoscintigraphy, an intraoperative mapping of the cutaneous lymphatics with vital dye is carried out at the time of surgical removal of the primary lesion. The vital dye, for example of blue color, is injected at the site of the lesion and tracked by blunt dissection until the sentinel node is reached. That node is now exclusively of blue color and readily identified. Thus, the sentinel draining lymph node of each primary melanoma is isolated and removed. By examining the sentinel nodes, for example by frozen section using routine hematoxylineosin histopathological techniques, as well as rapid immunohistochemical techniques, only those patients who have evidence of micrometastasis in the sentinel draining node are subject to subsequent lymphodenectomy. See generally, Morton D., Wen D-R, Wong J., et al. "Technical Details of Intraoperative Lymphatic Mapping for Early Stage Melanoma", Arch. Surg. 1992: 127:392–399; and "Lymphoscintigraphy in High-Risk Melanoma of the Trunk: Predicting Draining Node Groups, Defining Lymphatic Channels and Locating the Sentinel Node", R. F. Uren, et. al, J. Nucl Med 1993; 34:1435–1440.

The approach of Morton, et al., also has been undertaken to moderate the otherwise somewhat radical axillary lymph node dissection common in staging breast cancer. Through the utilization of the noted vital dyes in conjunction with the lymph drainage system from primary breast tumor, less radical sentinel node based procedures may result in adequate axillary staging and regional control. With the procedure, in general, a vital blue dye is injected into the breast mass and surrounding breast parenchyma. Following a relatively short interval, a transverse incision is made just below the hair bearing region of the axilla. Blunt dissection is performed until a lymphatic tract or duct leading to a blue stained node is identified. The lymph duct, having a blue color, provides a guide path leading to the location of the most proximal lymph node and thus the sentinel node. This sentinel node is excised and evaluated. While the procedure calls for considerable surgical experience and talent associated with the delicate task of following the blue duct (a ruptured dye-carrying duct can be problematic), the ability to identify a tumor-free sentinel lymph node will enable the surgeon to accurately stage metastasis-free breast cancer patients without subjecting them to the risks of radical dissection. The approach may also improve histologic staging by enabling the pathologist to focus on fewer lymph nodes. See generally Guiliano, A. E.; Kirgan, B. M.; Guenther, J. M.; and Morton, D. L., "Lymphatic Mapping and Sentinel Lymphadenectomy for Breast Cancer", *Annals of Surgery*, vol. 220, no. 3: 391–401, 1994, J. B. Lippincott Company.

For melanomas, it has been a more recent practice to identify the pertinent drainage basin or regional nodes along with an evaluation of the extent of lymph involvement with micrometastasis. A pre-surgical step undertaken in about 20% of investigational procedures concerning melanomas looks to carrying out of a gamma camera generated form of lymphoscintigraphy which gives the clinician a gross two-dimensionally limited image, generally showing the tumor site injection of a sulfur colloid labeled with technetium 99-m ($^{99m}T_c$) and, spaced therefrom, a region of radioactivity at the pertinent regional lymph nodes. The latter information at least confirms the path of drainage and the location of the proper drainage basin. Regional nodes then are removed and submitted for pathology evaluation.

Lymph node involvement in metastasis also has been the subject of investigation in other quite different forms of cancer such as colonic cancer. This has been through the utilization of a hand-held radiation responsive probe. U.S. Pat. No. 4,782,840 by Martin., M.D. and Thurston, Ph.D., entitled "Method for Locating, Differentiating, and Removing Neoplasms", issued Nov. 8, 1988, reviews the approaches of nuclear medicine for locating colonic tumor. The patent discloses al method for locating, differentiating, and removing neoplasms which utilizes a radiolabelled antibody in conjunction with the radiation detection probe, which the surgeon may use intraoperatively in order to detect the sites of radioactivity. Because of the proximity of the detection probe to the labelled antibody, the faint radiation emanating from occult sites becomes detectable because, in part, of the inherent application of the approximate inverse square law of radiation propagation. The procedure is known as the RIGS® procedure, RIGS being a registered trademark of Neoprobe Corporation, Dublin, Ohio. The RIGS system has been found to provide a unique identification of involved lymph nodes for staging evaluation. See, for example, Nieroda, C. A., et al., Surg. Gynecol. Obstet. vol. 169(1), 1989, pp 35–40. This RIGS lymph evaluation also may be employed with certain more minimally invasive procedures as described by M. W. Arnold, M. D., and M. O. Thurston, Ph.D., in U.S. Pat. No. 5,383,456, entitled "Radiation-Based Laparoscopic Method for Determining Treatment Modality" issued Jan. 24, 1995.

As an aspect of the RIGS system, the location of involved lymph material or neoplasm is carried out utilizing a statistical approach. With this approach, a background count rate of radiation emanation is developed, for example, at the aorta of the patient for an interval of time, for example, 5 seconds. A microprocessor-based control system then calculates a statistically significant value, for example a predetermined number of standard deviations of the basic count rate to derive a statistically significant threshold radiation count rate level. The ranging procedure is referred to by surgeons as "squelching". Operating in conjunction with that threshold level, the instrument provides the surgeon with audible cues representing that a high probability of tumor involvement is present at a location closely adjacent the forward window of the hand-held probe.

RIGS-based instrumentation, for example as described in Denen, et al., U.S. Pat. No. 4,801,803, entitled "Detector and Localier for Low Energy Radiation Emissions," issued Jan. 31, 1989, may be employed for detecting and "mapping" a lymph duct draining from a tumor or lesion. Additionally, the squelching procedure, heretofore employed to preset the instrumentation so as to locate otherwise undetectable tumor may be used as a guide to the sentinel node. However, the control unit and standard hand-held probe used with it initially were designed for a different type of use involving very faint levels of radiation. Performing with this very low level radiation, the instrumentation located labeled antibody present at the site of occult (often extremely small) tumor. By contrast, the radiopharmaceutical materials employed in sentinel lymph node location often are of a comparatively high intensity (count rate).

A system for tracking a radiopharmaceutical within a duct of the lymph system as it extends to the sentinel node within a regional node grouping which makes use of an adaption of the aforementioned squelching procedure is described in an Application, for U.S. patent, Ser. No. 08/543,032, entitled "Remotely Controlled Apparatus and System for Tracking and Locating a Source of Photoemissions," filed Oct. 13, 1995. Such tracking along the duct is a practical feature of the system by virtue of the determination and proof that radiation from that small vessel attenuates not according to the inverse square law of radiation propagation, which is a characteristic of point sources, but as an inverse first power.

In performing any surgical procedure, the surgeon must work within given time, parameters. Each time the squelch function is performed using the RIGS procedure, the surgeon is required to retain the probe in position over the tissue for a 5 second interval to determine a new threshold level. The above system utilizes two buttons which allow the surgeon to adjust the threshold level more quickly and thus locate the sentinel node more quickly. With the addition of the trim buttons, the sophisticated RIGS method is most useful in locating sources of extremely low radiation and detecting and isolating a node once its regional position is located. But even with the addition of the trim buttons, the threshold may only be adjusted within certain limits. The maximum manual adjustment range is approximately three times the square root of the two second equivalent of the last occurring five second standard squelching operation. Minimum value squelch background attainable is equivalent to 25 counts in a 5 second interval. In cases where the surgeon must perform the squelch function a number of times, a different technique is needed to more quickly adjust the threshold level, thus enabling the surgeon to more quickly map or survey a lymph vessel. This particular form of squelching technique necessarily involves working from a silent, i.e. no sound output, to a sound output. Then the procedure is reiterated until the probe face essentially is adjacent the sentinel node.

BRIEF SUMMARY OF THE INVENTION

The present invention is addressed to a system for detecting and locating sources of photon emissions emanating from tissue. Having an important application in connection with the tracking and location of a radiopharmaceutical migrating along a lymph duct and collecting at a lymph sentinel node, the system achieves a full scale readout approach with respect to both aural and visual cuing. In the latter regard, the system affords the practitioner a highly desired thresholding function which enhances the discernment of point source radiation as may emanate from a sentinel node. While this thresholding feature is, in itself, advantageous, it is further complemented by the addition of both pre-thresholding ranging and post-thresholding expansion of threshold attenuated signals. As a result, the full scale or pitch dynamic range of an aural cuing assembly such as a combination of a frequency generator and loudspeaker is made available. The practitioner is given the opportunity of adjusting the threshold, for example, between 5% (min) and 80% (max) of a count rate range and, notwithstanding an adjustment position at maximum percentage, the system still achieves full scale performance at its readouts.

To achieve this desirable performance, the control assembly of the system responds to detector outputs from a hand-held probe, for instance, utilizing an earlier-developed RIGS input control network to derive validated photon count signals of constant pulse width. Then, a converter network is employed to develop voltage levels which correspond to the rate of the received count data. Those voltage levels will occur within a frequency-to-voltage generator dynamic voltage range. The rate related voltage signals then are directed to a ranging network which achieves substantially full scale or dynamic range utilization of them for each of a plurality of count rate ranges. The resultant signals then we directed to a threshold network which employs a summing stage and a threshold signal generator, in turn, utilizing a variable resistor component to provide a threshold signal which, in effect, is subtracted from the range rate output level voltage at the summing stage. Through the utilization of a variable resistor approach, the thresholds may be manually varied to suit the instant requirements of the practitioner. However, to again achieve full scale performance, a post thresholding expansion stage is utilized which additionally employs a variable resistor component. By synchronizing the two variable resistor components, the threshold treated and attenuated output of the threshold stage is returned to full scale values to achieve full scale performance of the aural or audio as well as visual cuing devices of the system.

In one aspect of the invention, the simultaneous adjustment of these variable resistance components is carried out by two finger actuated switches which are located on the hand-held probe of the system.

Other objects of the invention will, in part, be obvious and will, in part, appear hereinafter.

The invention, accordingly, comprises the system and apparatus possessing the construction, combination of elements, and arrangement of parts, which are exemplified in the following detailed description.

For a fuller understanding of the nature and objects of the invention, reference should be had to the following detailed description taken in connection with the accompanying drawings.

BRIEF DESCRIPTION OF THE DRAWINGS

FIG. 2 is a sectional view taken through the plane 2—2 shown in FIG. 1;

FIG. 3 is a sectional view taken through the plane 3—3 in FIG. 2;

FIGS. 5A and 5B combine as labeled thereon to provide a block diagrammatic representation of the circuits employed with the control assembly and probe shown in FIG. 1;

DETAILED DESCRIPTION OF THE INVENTION

Figure 1:
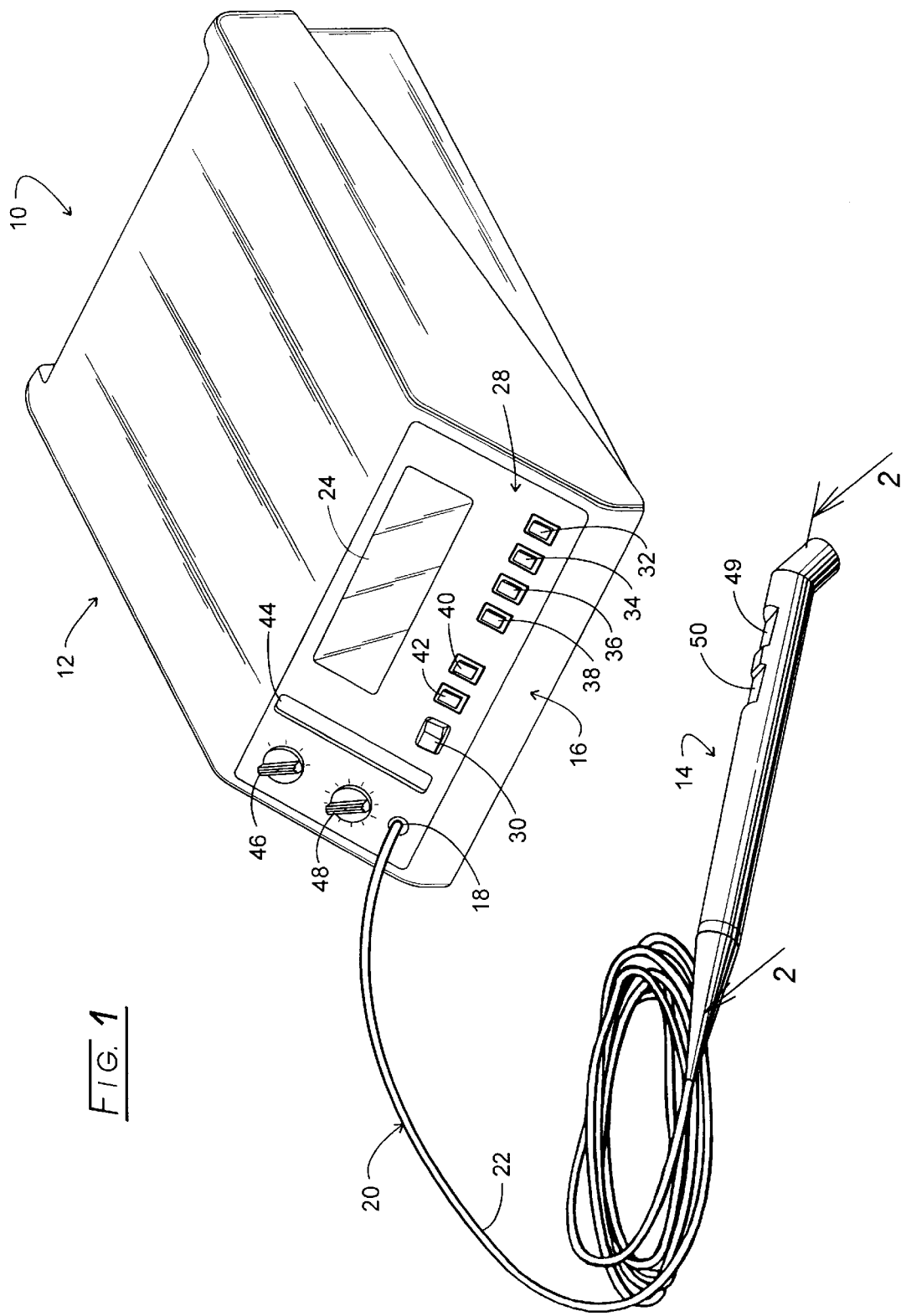
FIG. 1 is a pictorial representation of the system and instrumentation of the invention.

Referring to FIG. 1, a radioimmnunoguided system (RIGS™) incorporating the features of the invention is represented generally at 10. System 10 includes a control assembly or console 12 to which is coupled a probe or probe instrument represented generally at 14. The control console 12 is configured for both carrying out radioimmunoguided surgery and for tracking radiopharmaceuticals injected at the situs of a tumor to locate a lymph sentinel node. In the latter regard, the photon count evaluation, including lower threshold and upper limit windowing and discriminator functions of die RIGS system are commonly utilized That system is described, for example, in U.S. Pat. No. 4,801,803, entitled "Detector and Localizer for Low Energy Radiation Emissions" by Denen, Thurston, and Ramsey, issued Jan. 31, 1989, assigned in common herewith, and incorporated herein by reference. The forward face 16 of console 12 includes a coupling or connector 18 which provides for electrical signal communication and power supply association with the probe instrument 14 via a transmission assembly represented generally at 20 which includes a flexible cable 22. This cable implementation of the transmission assembly is a preferred arrangement for such transmission functions, however, other approaches will occur to those skilled in the art. Forward face 16 of console 12 additionally carries a relatively large liquid crystal display (LCD) readout 24, as well as an array of push type switches 28. This array of switches permits the microprocessor driven control assembly 12 to carry out an instructive or "user friendly" dialogue with the practitioner. In addition to a conventional on and off rocker switch 30, the switches provided at forward face 16 include such function selection switches as a count mode switch 32, a reset count switch 34, a background count or squelch switch 36, a sound control switch 38, and down and up incrementing switches shown, respectively at 40 and 42.

Also mounted at the forward face 16 of the console 12 are components dedicated to the lymph tracking features of the system 10. In this regard, a linear, segmented LED array 44 is included for the purpose of providing a visual cuing aspect as to peak count rate level. A range selection switch is provided at 46. Switch 46 permits the practitioner to select any of four count rate ranges to achieve full scale readouts. These ranges may, for example, be 0–1000 counts per second; 0–2500 counts per second; 0–7,500 counts per second; and 0–30,000 counts per second. Below the knob actuated range switch 46 is a knob actuated threshold control 48 which is used to provide a count rate threshold input which is a percentage valuation of any one of the count ranges established at switch 46. This thresholding is a variation of the background count or squelch procedures carried out in connection with switches 36 and 34. In this regard, the function of reset count switch 34 is to derive a count value over a preset interval, for example, 2 seconds. The background count switch 36 is employed in conjunction with reset count switch 34 to develop a statistical count value based upon a measured background count rate. For example, in the RIGS procedure, the probe instrument 14 initially is positioned in the vicinity of the heart or aorta in order to obtain a blood pool background count rate. The interval during which this rate is determined is, for example, five seconds. The microprocessor-based control system of console 12 then calculates a statistically significant value, for example a predetermined number of standard deviations of the basic background count rate to derive a statistically significant threshold radiation count rate level. This, for example, may be 3 sigma above the base count rate. The ranging procedure is referred to by surgeons as "squelching." Operating in conjunction with that threshold level in the RIGS procedure, the system 10 provides the surgeon with audible cues indicating that a high probability of tumor involvement is present at a location closely adjacent the position of the forward window of probe instrument 14. This squelching procedure also may be utilized in conjunction with the detecting and locating of sentinel lymph nodes in connection with breast cancer or melanoma studies or procedures. However, with the system 10, a dedicated adjunct system is provided for that purpose.

Probe instrument 14 is configured to provide a switching function which is utilized in conjunction with the noted sentinel node or lymph node tracking adjunct system. The probe device is described and claimed in copending application for U.S patent entited "Apparatus and System for Detecting and Locating Photon Emissions and Method of Fabrication with Remote Switch Control" by Olson and Thurston, Ser. No. 08/662,600, filed Jun. 13, 1996, assigned in common herewith, now U.S. Pat. No. 5,682,888, issued Nov. 4, 1997, and incorporated herein by reference. Two switches are provided on probe 14 as at 49 and 50 which afford the practitioner the opportunity to carry out the function otherwise carried out by threshold setting control 48. In general, where switches as at 49 and 50 are not provided with the probe 14 then the control 48 is utilized for a threshold setting.

FIG. 2 shows that the probe instrument 14 is configured having a unitary housing 60 with a hand graspable surface which extends between a forward end 62 and a rearward end 64. A detector assembly represented generally at 66 is coupled to the forward end 62 of housing 60, while the transmission assembly 20 is coupled to the housing 60 at its rearward end 64. Two planar switch actuating surfaces are formed integrally into the housing 60 as shown at 68 and 70. These surfaces 68 and 70 correspond with the respective switching functions 49 and 50. Looking additionally to FIG. 3, it may be observed that the surfaces 68 and 70 are machined into the housing 60 in a manner providing forwardly and rearwardly disposed bevels shown, respectively, at 72 and 74. Intermediate the surfaces 68 and 70, a beveled rib 76 is defined having a flat, upwardly disposed surface 78 establishing a rib height which falls below the external periphery of housing 60. The thus-defined switches 49 and 50 are readily tactilely identifiable to a practitioner.

FIGS. 2 and 3 reveal that the housing 60 is configured having an internally disposed switch receiving channel 80 which is open and accessible at the rearward portion of housing 60 through a cylindrical bore-formed cavity 82, as well as from a cylindrical bore formed cavity of shorter length at the forward end as seen at 84. Channel 80 is configured having an upwardly disposed switch contact surface 86 and a parallel planar oppositely disposed load surface 88. In general, the thickness of the housing material beneath surfaces 68 and 70 will range from about 15 mils to 20 mils and any resultant flexure upon switch actuation from those surfaces will be in a micro-inch range.

Positioned in abutting adjacency with switch contact surface 86 are the pressure-responsive surfaces of a two-component thin piezoelectric switch 90. The contact surface of the switch 90 is supported upon a stiff substrate, for example formed of FR4 material. The bottom of this material is a flat-oppositely disposed support surface having three terminal connections (not shown). With the arrangement, one switching component of the piezoelectric device 90 is located beneath surface 68 and the other beneath surface 70. Switches as at 90 are marketed by Wilson-Hurd, Inc., of Wausau, Wis., and have been described, for example, in Iten, U.S. Pat. No. 4,857,887, issued Aug. 15, 1989. Preferably, such switches are preloaded in compression to enhance their performance.

To retain the switch 90 compressively against the switch contact surface 86, a switch support assembly shown generally at 92 is provided. Assembly 92 is formed of two complementary wedges 94 and 96 formed of aluminum with matching sloping surfaces which serve to provide oppositely disposed parallel outer surfaces. Note that the outer surface of wedge 96 is in abutting adjacency with load surface 88 of the switch receiving channel 80. By moving wedge 96 forwardly and retaining wedge 94 in stationary position a compressive load may be developed against the piezoelectric switch 90 serving both to hold it in position and to provide a desired preloading. The two spaced piezoeloctric switching devices within switch 90 provide a voltage switching signal. Accordingly, a transmission lead is provided for each of these switches in addition to an instrument ground. These three leads, one of which is revealed at 98, are directed to two switch detection circuits mounted upon a circuit board 100. Circuit board 100 carries two current deriving circuits, one for each of the piezoelectric switch components of the switch 90. The circuits mounted upon board 100 function to provide a current value superimposed upon the +12 V supply input provided to the probe 14 from the cable 22. Such current signals are directed via one of the two wires of lead grouping 102 to a connector circuit board 104 mounted across cavity 82.

Located adjacent to a coextensive switch switch receiving channel 80 is a detector signal channel 110 extending in open accessing relationship between cavities 82 and 84, and configured to receive a printed circuit board 112 serving to carry a preamplification circuit. This preamplification circuit associated with circuit board 112 functions in connection with a lead array 114 which is seen in FIG. 2 to extend rearwardly for connection to circuit board 104. It may be observed that channels 80 and 110 are configured to provide a shield wall between them. Accordingly, the important signals generated at the preamplifier circuit board 112 and the signals carried by the lead array 114 are shielded from any interference evoked from the switching components.

Circuit board 112, carrying the preamplifier function of probe 14, is supported from the detector assembly 66. Assembly 66 extends outwardly from forward end 62 to housing 60 as a consequence of a union of forward end 62, which is canted at an angle of 15° with respect to the centrally disposed axis 116 of housing 60, and the corresponding 15° cant of a short connector tube 118. Connector tube 118 is connected to the housing 60 at end 62 by a weld and is cylindrically shaped and canted at 30° with respect to axis 116. The tube 118 is necked down such that it may receive an end cap 120, the circular forward face of which at 122 is formed of a material transparent to the radiation of interest, i.e. constitutes a window. Also mounted upon the tube 118 is a generally cylindrically shaped detector mount 124 having a cylindrical cup-shaped cavity formed therein which receives a crystal detector shown in phantom at 126. In general, the mount 124 is formed of material attenuating radiation and the sides of the cavity formed therein extend forwardly such that only a forward face of the crystal 126 may receive impinging radiation through the window 122. In general, a cadmium telluride crystal detector is employed for the instant purpose. This type crystal requires the application of ground at its forward face immediately adjacent window 122, and the application of a bias input at its opposite or inwardly disposed surface. Such bias is applied from the preamplifier at circuit board 112 through leads extending along a cylindrical channel shown in phantom at 128. FIG. 2 further reveals what the circuit board 112 carrying a preamplifier is attached to the detector mount 124 at an outwardly depending cylindrical stud 130.

Now looking to the transmission assembly 20, it may be observed that rearward end 64 of housing 60 is connected to a cylindrical rear cap 132. Rear cap 132 is intimately coupled with an elongate conically shaped relief component 134 formed of medical grade silicone which surmounts and seals against cable 22.

Figure 4:
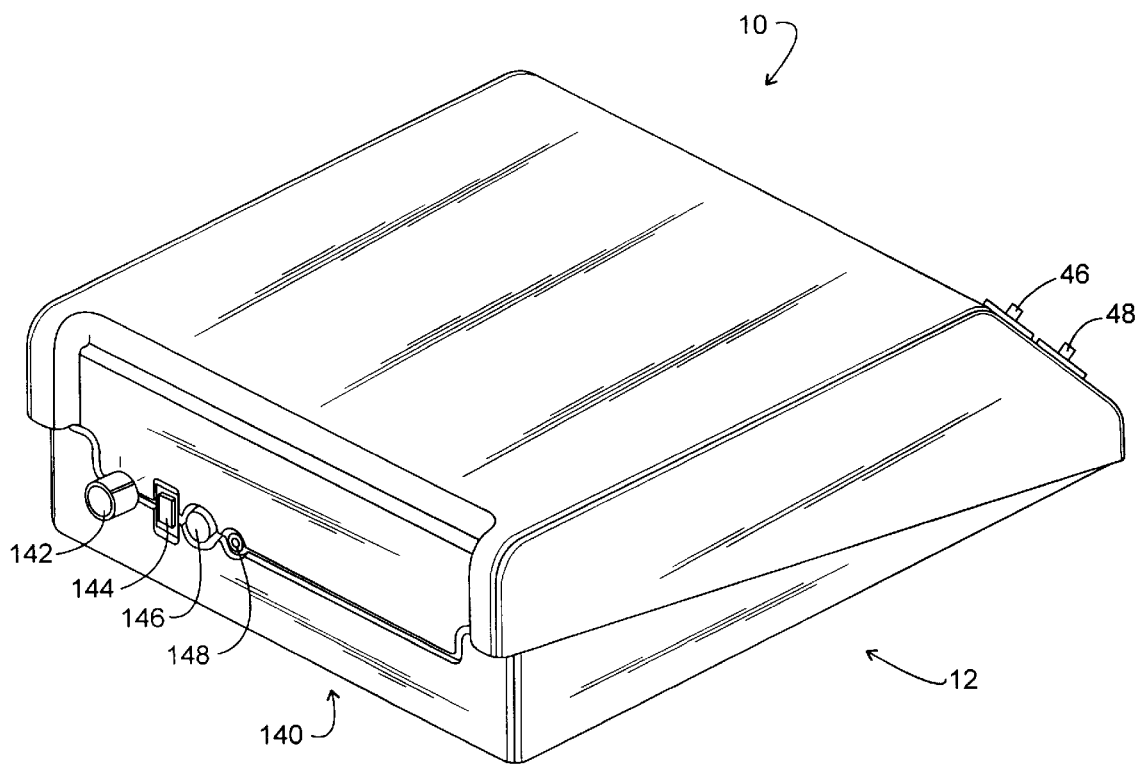
FIG. 4 is a perspective rear view of a console illustrated in FIG. 1.

Referring to FIG. 4, a view of console 12 again is provided, however revealing the structuring of the rear wall 140 thereof. At this wall 140, there is located a mode selection switch 142 which is manually actuated to either of two positions, one electing that the system 10 operate in its standard RIGS mode, and the other electing that the system 10 operate in conjunction with the adjunct system for carrying out sentinel node detection procedures and the like. Adjacent switch 142 is a pushbutton type calibration switch 144 which provides for carrying out a calibration of the system. Also mounted at the wall 140 are a fuse access assembly 146 and a battery charger input connector 148. Switches 142 and 144 are located at the rear wall 140 instead of the forward face 16 to avoid any inadvertent actuation of them.

Figure 5B:
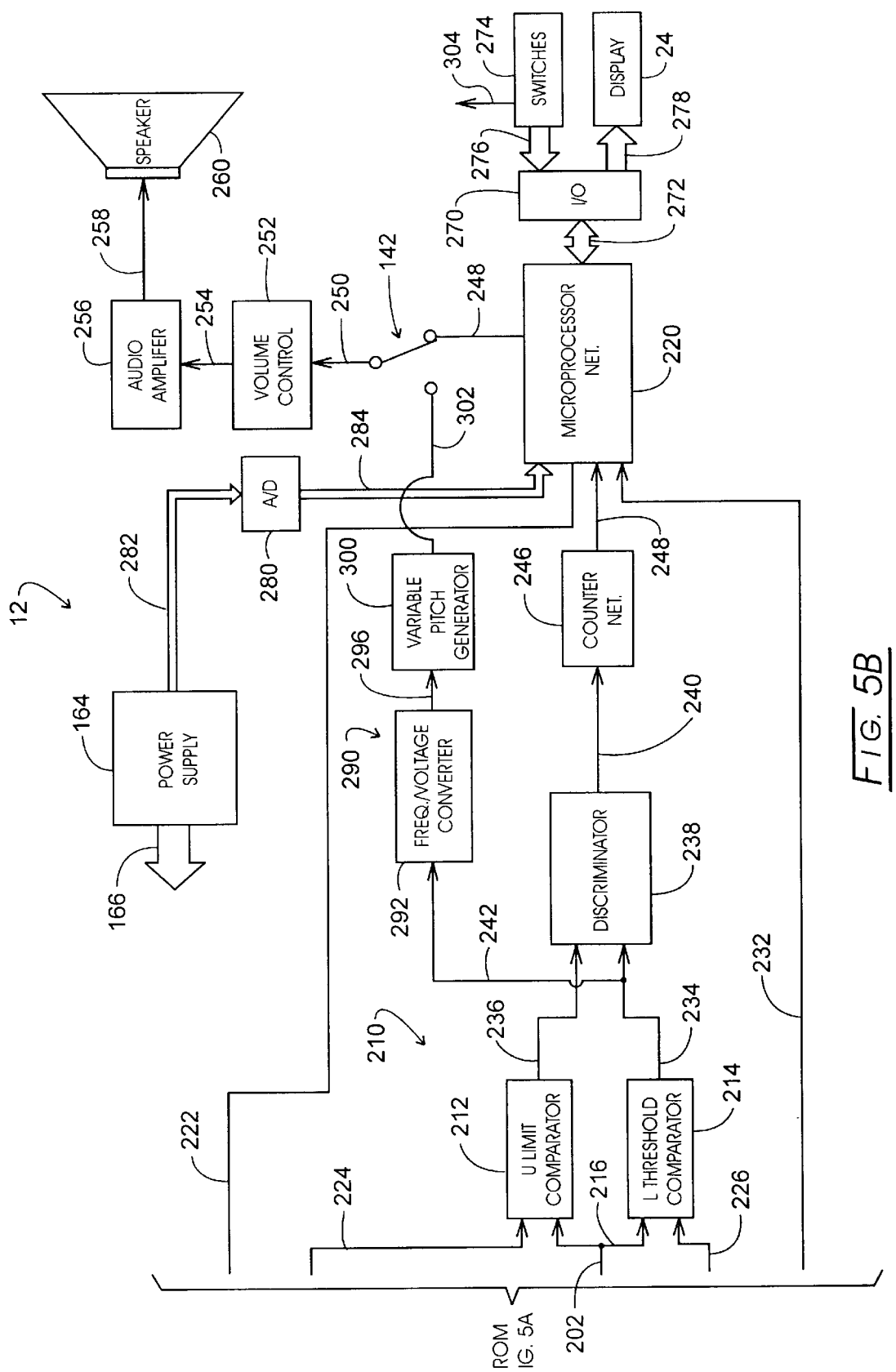

Referring to FIGS. 5A and 5B, a block diagrammatic representation of the circuitry employed with the system 10 is portrayed. These figures should be considered in mutual adjacency in the manner labeled thereon. In FIG. 5A, a crystal such as a cadmium zinc telluride crystal suited for mounting within the detector mount 124 is represented with the earlier numerical identification 126. Crystal 126 is shown having one face coupled to ground through line 152, while the opposite, biased face thereof is coupled via lines 154 and 156 to a bias filter represented at block 158. The input to filter 158 is represented at line 160 as being applied through the cable as described earlier at 22, which number reappears in the instant figure. The bias input is seen, as represented at line 162, emanates from a multi-output power supply shown in FIG. 5B at block 164. These various outputs are represented, in general, by an arrow 166 extending from block 164.

Returning to FIG. 5A, line 154 from the crystal 126, carrying detector outputs corresponding with radiation emissions impinging upon the crystal, is seen to extend to an integrator stage represented at block 168. This integrator stage 168 forms part of the preamplification function mounted at circuit board 112. The integrated valuation of detected radiation emissions then is shown directed as represented by line 170 to a driver amplification network shown at block 172. A preferred preamplification circuit comprised of blocks 168 and 172 is described in U.S. Pat. No. 5,441,050 by Thurston and Olson, issued Aug. 15, 1995, entitled "Radiation Responsive Surgical Instrument", which is assigned in common herewith and incorporated herein by reference. A d.c. power supply is provided from the power supply represented at block 164 and arrow 166 (FIG. 5B) for the preamplification function. This power supply is directed, as represented at line 174, to a probe current network represented at block 176. Under microcomputer control as represented at line 178, the network 176 develops signals, for example, determining whether the probe instrument 14 has been properly connected to the console 12. Delivery of the d.c. power supply for the preamplification function is represented at lines 180 and 182. Line 182 forms a component of flexible cable 22. Connected with line 182 is one line of the output of the piezoelectric switch 90 and associated circuitry at circuit board 100 (FIG. 2) as represented at line 184. The second line from that board is shown at line 186 which is connected to instrument ground at line 188. This ground is generated from the power supply at block 164 (FIG. 5B) and arrow 196 (FIG. 5A), and is represented by an additional line 190 within the control assembly 12. The probe switches and coding circuitry are represented in FIG. 5A at block 192. In general, when either of these switch components of the piezoelectric switch 90 is actuated, a switch voltage signal is generated which is directed to a current deriving voltage comparator circuit having an output coupled, as represented at line 184, with the power supply input line 182. The switch voltage signal generated by the piezoelectric switches, performing with comparator circuit, functions to impose a current signal of predetermined amplitude at lines 182 and 180, which is detected by probe switch logic circuitry represented at block 194. The logic represented at block 194 includes a monitoring amplifier stage and level comparator circuit which function to provide switch input signals corresponding with the actuation of either of the switch components 98 or 50 derived by the application of finger pressure upon the respective switch actuating surfaces 68 or 70. These switching input signals are provided, respectively, at lines 196 and 198. With this implementation of the probe switches as represented at block 192 as well as the probe switch logic represented at block 194, the pre-existing power supply line of flexible cable 22 is utilized to carry the switch signal and no additional wiring is required for that component of the system 10.

The preamplification stage is a signal treatment circuit which provides count outputs which are presented along line 200 of cable 22 for introduction to the control assembly 12, the corresponding signal carrying line of which is shown at line 202. Line 202 extend to the input of an energy window network represented in FIG. 5B in general at 210 which functions to evaluate the count outputs to derive validated photon count signals. Looking to FIG. 5B, it may be observed that the energy window network 210 includes an upper limit comparator represented at block 212, as well as a lower threshold comparator represented at block 214. The count output or photon event signals at line 202 are submitted simultaneously to each of these comparator functions 212 and 214, as represented at line 216. Correspondingly, the comparison values or limits associated with the upper limit comparator 212 are applied from a digital-to-analog converter (DAC) seen in FIG. 5A at block 218. Converter 218 is under the control of a microprocessor network represented at block 220, such digital control to device 218 being asserted as represented at line 222. Thus, the upper limit value asserted at the comparator 212 is provided at line 224, from DAC 218. Correspondingly, the lower threshold value for comparator function 214 is asserted from DAC 218 via line 226. FIG. 5A, also reveals that the signals at line 202 are directed, as represented at line 228, to a pulse acquire function represented at block 230. Network 230 functions, when activated by the microprocessor function 220, to acquire the value of the highest pulse amplitude witnessed at line 202. Periodically, this information then is transmitted to the microprocessor function 220 as represented by line 232. Representing a form of peak detector, the network 230 sometimes is referred to as a "snapshot circuit".

With the arrangement shown, the probe 14 assemblage derives count outputs in response to photon emissions which are confronted at the forward face of crystal 126. Those count outputs will have an amplitude corresponding to the energy of interest of the photon emissions. Additionally, the signals may represent spurious phenomena such as cosmic rays and the like. Accordingly, the energies of the count outputs or amplitudes thereof are evaluated at the energy window network 210 as seen in FIG. 5B. The lower threshold comparator function 214 will promulgate a pulse at line 234 when the signal asserted thereat exhibits an amplitude of value equal to or above a threshold value established, as noted above, from line 226. Correspondingly, the count output signals from line 216 will be evaluated by the upper limit comparator function 212 such that when the count output signal exhibits an amplitude of value above the upper limit value established from line 224, a pulse will be promulgated at line 236. For the RIFS component of the system 10 outputs from lines 234 and 236 then are directed to the input of an asynchronous, sequential, fundamental mode discriminator circuit represented at block 238. Circuits as at block 238, while being sequential in nature, are not synchronized in any way with a clock signal. Such circuits as at block 238 are described in U.S. Pat. No. 5,475,219 by Olson, entitled "Validation of Photon Emission-Based Signals Using an Energy Window Network in Conjunction with a Fundamental Mode Discriminator Circuit", issued Dec. 12, 1995, assigned in common herewith, and incorporated herein by reference. The discriminator function represented at block 238 serves to generate photon event outputs for count associated signals in the form of finite pulses at line 240. Such pulses occur with the presence of a count output signal at line 202 which represents a photon emission which is valid from the standpoint of the energy range of interest associated with it.

The pulsed signals at line 240 are provided to a counter network represented, at block 246. These pulses at line 244 are counted by the network 246, whereupon, as represented at line 248, count data is submitted to the microprocessor network 220 for statistical analysis. The function of counter network 246 may be implemented in software as described in the above-referenced U.S. Pat. No. 4,889,991. Microprocessor network 220 performs under a variety of operational modes depending upon the user inputs to the function switches at array 28 (FIG. 1) and calibration switch 144 (FIG. 4). In general, it functions to provide outputs to two output components, one aural type generated from a speaker, and the other a visual output at display 44. Generally, a "siren" type of signal manifested with a predetermined frequency variation is asserted as represented by line 248 through mode switch 142 and line 250, to a volume control function represented at block 252, whereupon the volume adjusted signal is directed, as represented at line 254, to an audio amplification circuit represented at block 256. The circuit at block 256, in turn, as represented at line 258, drives a speaker 260. With the noted siren arrangement, the frequency output from speaker 260 increases with an exponential change from 20 Hz to 1200 Hz when the average count rate determined by system 10 exceeds a preset threshold level which is statistically significant over background count rates. The siren mode is accessed by the user from console 12 by sequentially actuating switch 36 then switch 34. This siren mode of performance is described in detail in the above-referenced U.S. Pat. No. 4,889,991, by Ramsey and Thurston.

Microprocessor network 220 performs in conventional fashion with an input/output network as represented at block 270 and dual directional arrow 272. This input/output port function 270 provides for appropriate scanning of pertinent console 12 mounted switches as represented at block 274 and arrow 276. The output port also drives the display 24 again represented by the same numeration in block form, as represented by arrow 278. Further, the microprocessor network 220 may be employed to monitor the performance, of the power supply represented at block 164. This is shown being carried out by the interaction of the microprocessor network 220 with an analog-to-digital converter represented at block 280 and having an association represented by arrows 282 and 284. The converter 280 functions to digitize analog values at the power supply 164 for submittal to microprocessor network 220.

Components of the adjunct system of system 10 are represented in general at 290 in FIG. 5B. The components of system 290 include a frequency-to-voltage converter represented at block 292 which responds to the count associated signals from the lower threshold comparator at block 214 as represented at lines 234 and 242 to provide a rate output level signal corresponding with the frequency of those count associated signals at line 296. This signal will be provided as a d.c. voltage level which extends within a dynamic range of, for example, 0 to 2.5 volts. That signal then is directed to a variable pitch generator function represented at block 300. The function at block 300 serve to provide the noted initial ranging feature and a count rate thresholding feature which my be controlled from knob 48 or the up/down switches 49 and 50 (FIG. 1). Additionally included in the function 300 is a post thresholding amplification network having a gain corresponding with the threshold level value to permit full scale performance of the speaker 260 and linear LED array 44 (FIG. 1). The output of function 300 is shown at line 302 extending to one terminal of switch 142. Microprocessor network 220 continue to provide volume control during the operation of generator function 300 in response to actuation of switch 38 (FIG. 1). An output represented at arrow 304 win be seen to extend to a "beep" generator which is part of the variable pitch generator shown at block 300 and which provides an auxiliary audible switch feedback for the user. This beep generator is further described in reference to FIG, 6.

Figure 6:
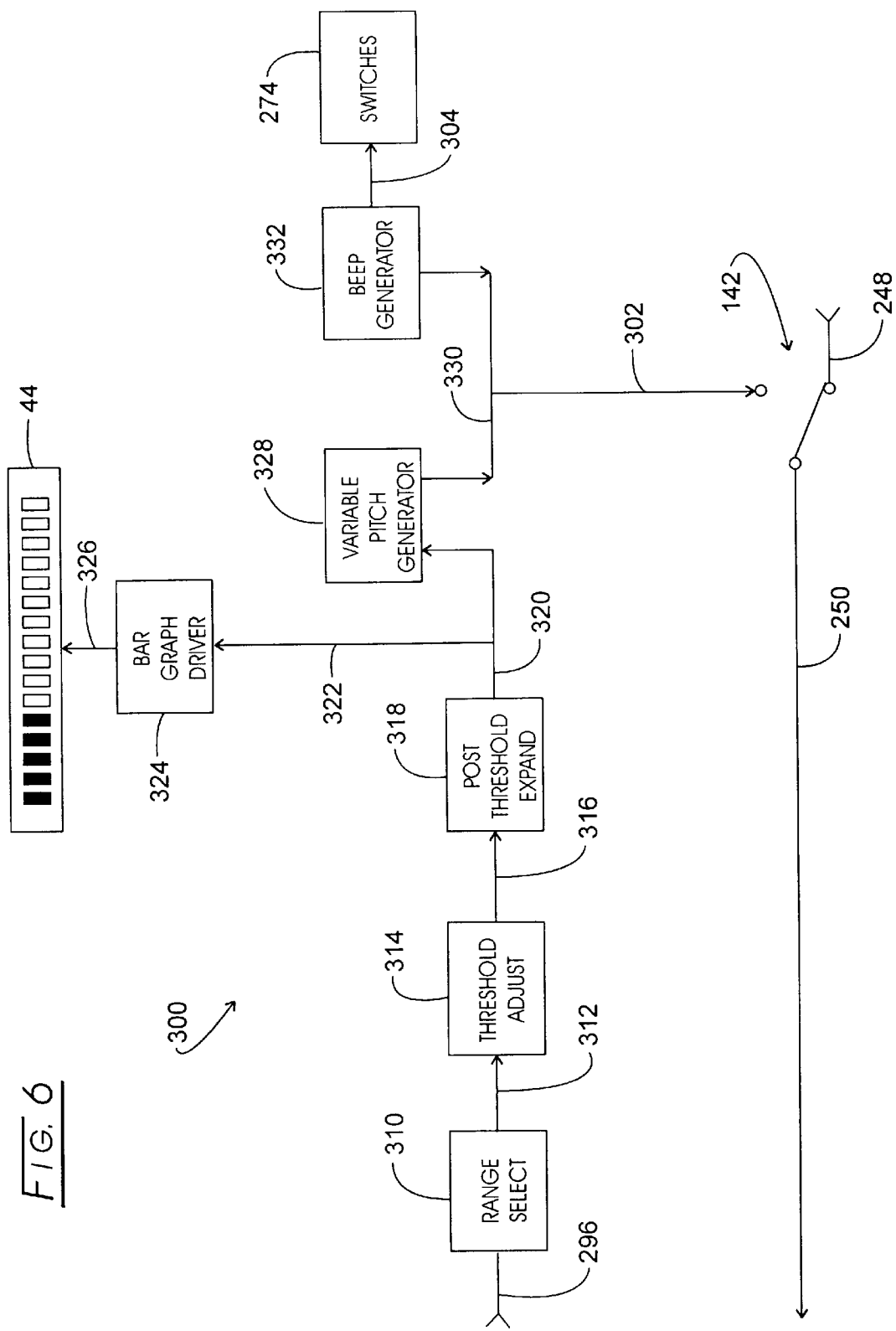
FIG. 6 is a block diagram showing variable pitch generator components of the system of the invention.

Referring to FIG. 6, a block diagrammatic representation of the generator function 300 is provided. The figure reveals that the output from the converter network 292 at line 296 is directed to a range select function represented at block 310. Function 310 provides for the earlier-described selection of ranges of counts per second such that an initial approach is taken to derive full scale drives for the visual and aural cuing components, i.e. LED array 44 and speaker 260. Upon selecting an appropriate range, the range adjusted signal level is directed, as represented at line 312 to the input of a threshold network represented at block 314. At block 314, a threshold is established with respect to the incoming signal at line 312 which represents a percentage of full scale or full dynamic range of that signal. Additionally, minimum and maximum values to which a threshold percentage can be set are developed. Without more, where high thresholds are employed, the signal level available for developing a drive for the LED array 44 or speaker 260 would be inadequate. A minimum threshold level is imposed to avoid sound outputs resulting from environmental noise. Such noise essentially is always at hand being found to be stronger in some geographic areas than others. The adjusted count rate signal at line 316 is directed to a post threshold amplification network represented at block 318. Network 318 is configured having a gain which corresponds with the threshold level value set at function 314 such that it carries out an amplification of the adjusted count rate signal at line 316 to provide an amplified count rate signal at line 320 which lies at levels within a predetermined output dynamic range. That dynamic range is established by the aural cuing and drive demands of the LED array or bar graph 44. In this regard, line 320 is tapped at line 322 and the signal thereat is directed to a bar graph driver function represented at block 324. Driver 324 then drives the array 44 as represented at line 326. Line 320 also is seen directed to a variable pitch generator represented at block 328 which functions to produce a drive signal at line 330 which is directed to line 302 which will produce a speaker drive output at a pitch corresponding with the drive signal asserted thereat and which lies between a zero pitch level and a maximum pitch level which corresponds with the noted dynamic range which is maintained. Because for the present embodiment, the microprocessor driven aural feedback from operation of the switches 274 is not present, an additional beep generator is provided as represented at block 332 which functions to generate a beep via line 302 at such time as any one of the switches 274 are actuated by the operator. Line 302 is reproduced from FIG. 5B as well as the designation for switch 142, line 248, and line 250.

Figure 7A:
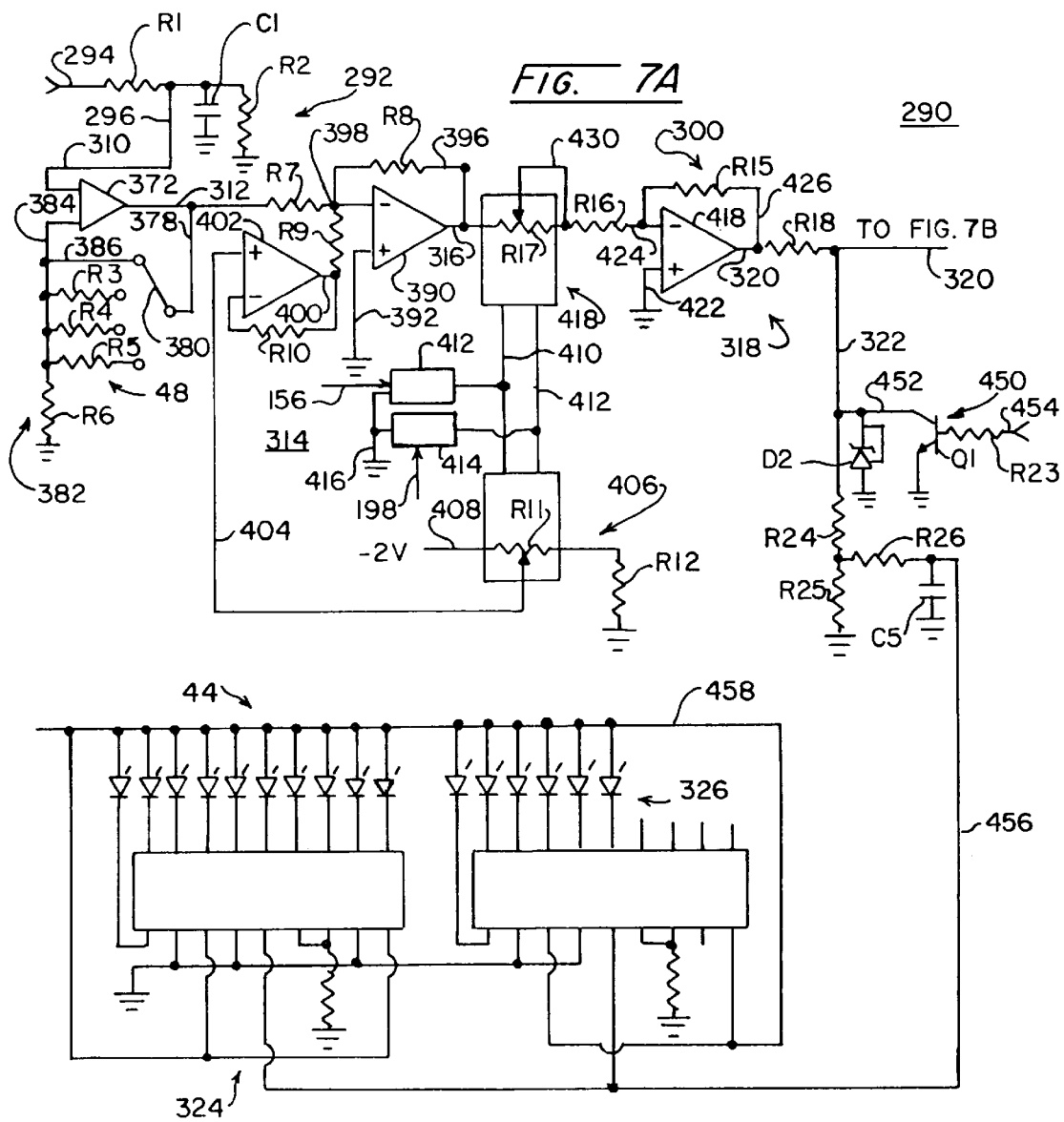
FIGS. 7A and 7B combine as labeled thereon to provide an electrical schematic diagram of the components of the system of the invention.
Figure 7B:
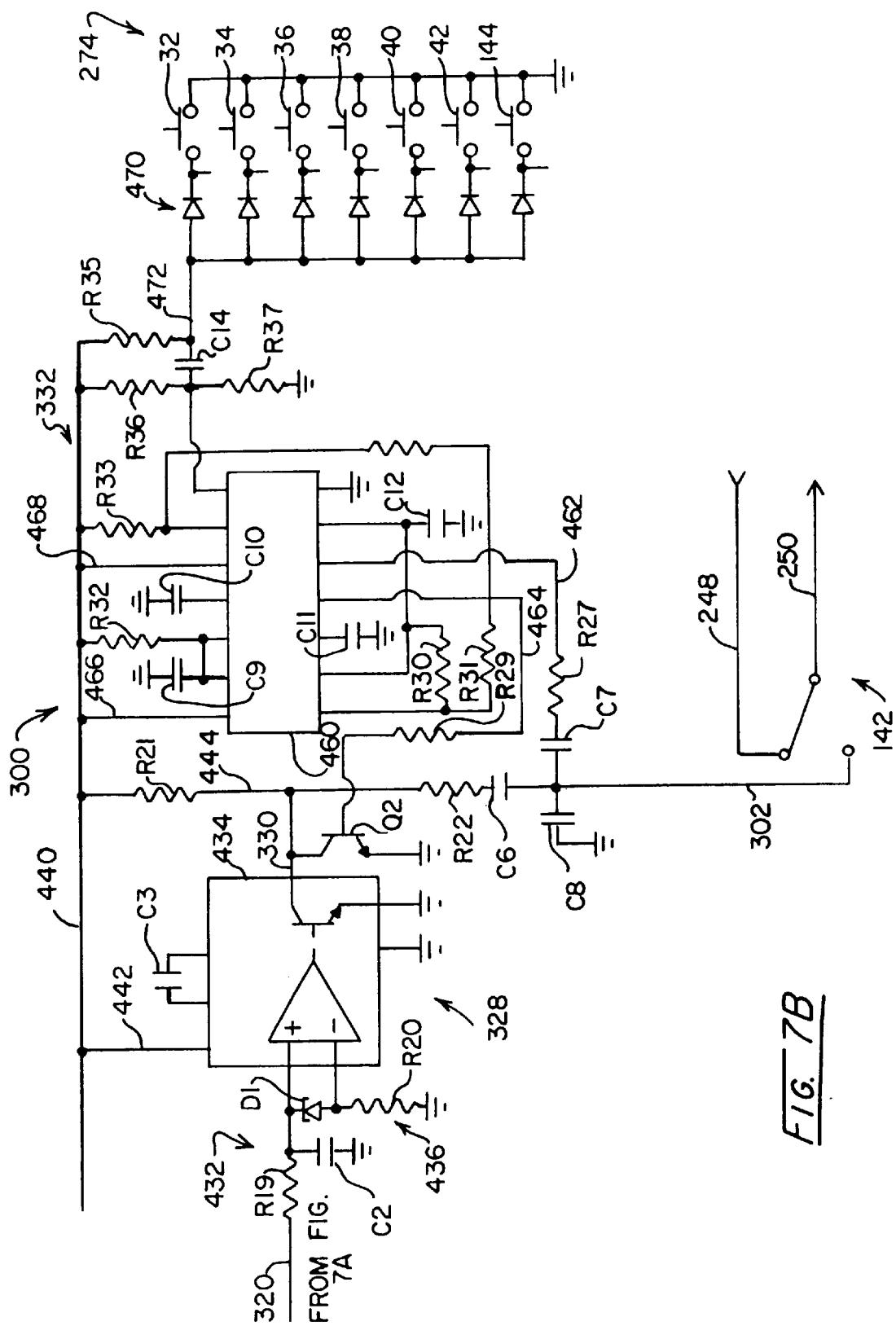

Referring to FIGS. 7A and 7B, an electrical schematic drawing is provided describing the adjunct system 290. These figures should be considered in mutual adjacency in the manner labeled thereon. In FIG. 7A, the frequency-to-voltage converter 292 is again identified by that numeration. Network 292 responds to the count associated signals produced at line 294. It may be recalled that these signals are in pulse form, each pulse having a constant duration. Because of this constant duration, a count rate is derived as a d.c. level with considerable simplicity. In this regard, network 292 includes an RC integrator circuit including resistors R1 and R2 performing in conjunction with an integrating capacitor C1. In general, the network will exhibit a time constant of about one second to provide an output level signal corresponding with the frequency of the count associated signal at line 296. Network 292 carries out its conversion function with substantial linearity. Line 296 is seen directed to one input of an operational amplifier 372 which is one component of a range selection stage represented generally at 310. Stage 310 performs in conjunction with earlier-described switch 248 which is identified in schematic form with the same numeration. It may be recalled from the discussion in connection with FIG. 1 that four count rate ranges are established with the function 300. To carry out this ranging procedure, the output of amplifier 372 at line 312 is coupled via line 378 and wiper arm 380 of switch 248 to a range selected resistance value derived from an array of resistors represented generally at 382 to the opposite input of amplifier 372 as at line 384. The array 382 includes resistors R3–R6, as well as line 386. Accordingly, by connecting line 380 with a selected resistance value, the gain of amplifier 372 may be adjusted. This permits the full dynamic range or full scale of the voltage output from converter 292 to be used in developing the drives for speaker 260 and LED array 44. Such a ranging feature is the initial component in achieving full scale drive for the cuing devices 44 and 260 within a system which employs thresholding.

The count range adjusted rate output level signal at line 312 then is directed to a threshold network represented generally at 386. Network 386 functions to impose a select threshold level value upon the signal at line 312. That threshold level value will correspond with a percentage value of the count associated signals. In this regard, should the selected count range be from 1 to 1000 counts per second (cps), then a 70% threshold might be selected either by adjustment of knob 48 or through the utilization of the switches 49 and 50 of probe 14. The result is an adjusted count rate signal. Preferably, the selection of the threshold level percentage for any of the four ranges is an adjustable one under the selection of the practitioner and will fall within minimum and maximum available threshold percentages. Preferably, those minimum and maximum values will be about 5% as a minimum percentage value and 80% as a maximum percentage value.

Network 386 includes a summing stage formed with an inverting operational amplifier 390. The inverting input to device 390 is coupled to line 376 which incorporates a resistor R7. Correspondingly, the non-inverting input is coupled to ground via line 392 and the output thereof at line 316 is coupled to a feedback path including line 396 and resistor R8. Line 396 additionally extends to a summing node or summing input 398, which is coupled through a resistor R9 to the output line 400 of a buffer 402 configured as a unity gain operational amplifier having a feedback path incorporating resistor R10 coupled to its negative input. The positive input to buffer 402 is coupled via line 404 to an adjustable potentiometer represented generally at 406. Potentiometer function 406 is coupled to a negative voltage supply, i.e. −2 volt at line 408 and is schematically portrayed as having a resistor R11 tapped by a wiper arm associated with line 404. Line 408 also extends through resistor R12 to ground. Device 406 may be a mechanical potentiometer which is actuated or adjusted from knob 48 (FIG. 1) or may be an electronically adjusted potentiometer or rheostat. For example, for the latter type of component, a type DS1669 dual pushbutton configuration electronic digital rheostat marketed by Dallas Semiconductor, Inc. may be employed. For such devices, a low true pulse applied to the up contact input line 410 will provide the equivalent of an upward movement of the wiper position in terms of adding resistance. Correspondingly, low true input from line 412 will cause an effective downward movement of the wiper position at resistor R11. Where actuation of the device 406 is from the probe switches 49 and 50, the signals from the probe will result in corresponding outputs at lines 196 and 198 as a result of functioning of the probe switch logic at block 194 (FIG. 5A). This logic then is converted to a contact closure to ground via the respective solid-state switching functions represented at respective clocks 412 and 414. These functions 412 and 414 are shown having a ground coupling at line 416.

Buffer 402 functions to protect the potentiometer 406 from overloading and is configured having a unity gain. Similarly, resistors R7–R9 are of equal resistance value to provide a unity gain for the summing amplifier 390. With the arrangement, the negative threshold level value asserted at the summing node or input 398 subtracts from the incoming range adjusted rate output level signal to provide the earlier-noted adjusted count rate signal at line 316. Without more, the remainder of that signal will be unable to provide a full scale drive to the cuing devices. Accordingly, post thesholding amplification network 318 is provided. This network 318 includes an operational amplifier 418 having, an adjustable gain which corresponds with the threshold level imposed in conjunction with the adjustment of potentiometer 406.

The output of amplifier 418 is provided a line 320, while the positive input thereto is coupled to ground via line 422. The input to device 418 is provided at line 424. The gain of amplifier 418 is derived from the configuration of resistor R15 within feedback path line 426, resistor R16 within line 424, and resistor R17 which is the variable resistor of another potentiometer represented in general at 418. The wiper arm of this potentiometer or variable rheostat is represented at line 430 which, in turn, is coupled to feedback line 426 through resistor R16. The input to potentiometer 418 and its resistor function R17 is provided from line 316 carrying the noted adjusted count rate signal. Where potentiometer function 418 is implemented as a mechanical device, then it is ganged upon a common shaft with the mechanical implementation of potentiometer 406. With that arrangement, then the gain at stage 318 corresponds with the threshold level value at stage 314 and the adjusted count rate signal then is amplified to provide an amplified count rate signal at line 320, which restores the signal dynamic range to provide full scale drives to the cuing devices.

Where the potentiometer function 418 is implemented electronically, then a noted type DS1669 device identical to that employed at 406 may be utilized. However, just as the mechanical implementation requires a common shaft for synchronization between these two devices, the electronic equivalent is required. Accordingly, it may be noted at lines 410 and 412 receiving the up and down signal inputs are common to both of these devices 406 and 418. When this electronic implementation is utilized, it is necessary that prior to each, use, they be zeroed out by actuating them down to their lowest functional potentiometer resistance position.

The output of stage 318 at line 320 extends through a resistor R18 and, as seen in FIG. 7B, introduces the post threshold amplification based signal to a filter represented generally at 432 comprised of resistor R19 and capacitor C2. Filter 432 functions to smooth the rate of transition of signals at line 320. Line 320 continues to introduce the now filtered drive signal to the variable pitch generator function 328. Function 328 is structured in conjunction with a voltage-to-frequency converter 344 which may be provided as a type AD654 voltage-to-frequency converter marketed by Analog Devices, Inc. Device 434 consists of an input amplifier, a precision oscillator system, and a high current output stage. It employs a single RC network to set-up any full scale frequency range, such network including the capacitor C3. The input to device 328 is clamped by a clamping network represented generally at 436 and comprised of Schottky diode D1 and resistor R20 which is coupled to ground. Clamping network 436 functions to protect the device 434 in the event that threshold negative voltages are asserted, a condition which may occur, for example, if no signal occurs at line 312. A regulated power supply is seen provided to device 434 from lines 440 and 442. It may be observed that output line 330 also is coupled to line 440 via line 444 incorporating resistor R21. Line 444 extends to line 302, which, in turn, incorporates resistor R22 and coupling capacitor C6. Line 302, in turn, functions as one input to switch 142 which selectively directs the frequency-based signal at line 302 via line 250 to the aural cuing devices.

Returning to FIG. 7A, it may be observed that line 320 is tapped by earlier-described line 322 which is directed to the bar graph driver 324. A clamping and protective network 450 is coupled to line 322. This network 450 includes a Zener diode D2 connected to line 322 via line 452 and to ground. Diode D2 clamps the maximum voltage level at line 320 to the earlier-noted 2.5 volts to avoid overdrive into device 434 (FIG. 7B). Additionally coupled to line 452 is the collector of NPN transistor Q1, the emitter of which is coupled to ground. A line 454 incorporating base resistor R23 is additionally provided in network 450. Transistor Q1 is turned on from line 454 to hold line 322 at ground by the microprocessor function 220 at start-up. This start-up delay will be maintained for about 10 seconds.

Line 322 also is seen to extend to instrument ground and incorporates divider resistors R24 and R25, the connection between which is tapped by line 456 which extends to the LED array or bar graph driver function 324. A filter comprised of resistor R26 and capacitor C5 is seen coupled with line 456. The driver function 324 is comprised of two type LM3914 LED drivers. Leads to these devices again are represented at array 326 and it may be noted that only 16 of the available driver components are utilized by the LEDs 44. Adjustment for this is made by incorporating the above-described divider resistors R24 and R25. The array of LEDs 44 are coupled to regulated 3.3 V power supply at line 458 and are energized by being coupled to instrument ground.

Returning to FIG. 7B, the beep generator 332 is represented in general by that numeration and is seen to include a dual timer component 460. Device 460 May be provided, for example, as a type TLC556 marketed by Texas Instruments. Device 460 incorporates two oscillators, one of which functions to provide an 800 Hz output to line 302 by connection thereto from line 462. Line 462 is seen to incorporate a resistor R27, coupling capacitor C7, and a filtering capacitor C8. The second oscillator of device 460 provides a beep interval function of 50 milliseconds. To avoid conflict of this frequency generator with device 434, the collector electrode of an NPN transistor Q2 is coupled to line 330 while its emitter is coupled to ground. The transistor is turned on by device 460 from line 464 incorporating base resistor R29. Power is supplied to device 460 via lines 466 and 468, and it is configured for the noted frequencies by capacitors C9–C12 and resistors R30–R33. Device 460 is actuated from the earlier-described switches 32, 34, 36, 38, 40, 42, and 144. Those switches are reproduced in FIG. 7B in conjunction with an array of ORing diodes represented generally at 470. With the actuation of any one of these switches, a low true signal is supplied to device 460 via line 472 which is configured having a coupling capacitor C14 and resistors R35–R37.

Figure 8A:
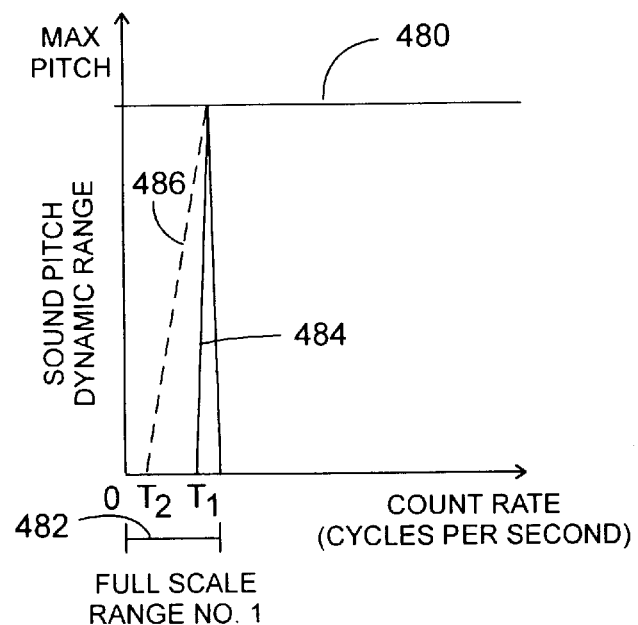
FIGS. 8A through 8D are graphs illustrating the ranging, thresholding and post thresholding features of the system of the invention.

Turning now to FIGS. 8A–8D, an illustration of the performance of the adjunct system in connection with the ranging feature 310, the threshold adjustment 314, and the post threshold expansion function 318. In FIG. 8A, a condition representing the lowest range, i.e. 0 to 1000 is represented. The vertical axis of this graph shows the sound pitch dynamic range from 0 to a maximum pitch value at line 480. The horizontal axis represents count rate in cycles per second. For this first range, full scale will be as represented at the distance 482 along the horizontal axis. Where the threshold adjustment function 314 calls, for example, a threshold setting of 70% of full scale, that value will be at position $T_1$. Thus, no sound will be heard until that threshold value in counts per second is reached. When it is reached, however, the full dynamic range of pitch output may be heard as represented by 484. Similarly, if the threshold setting is at 20% of full scale, then the system will perform as represented by dashed line 486, again providing the opportunity for a full excursion of the available pitch from threshold setting $T_2$ to the top of this particular range setting.

Figure 8B:
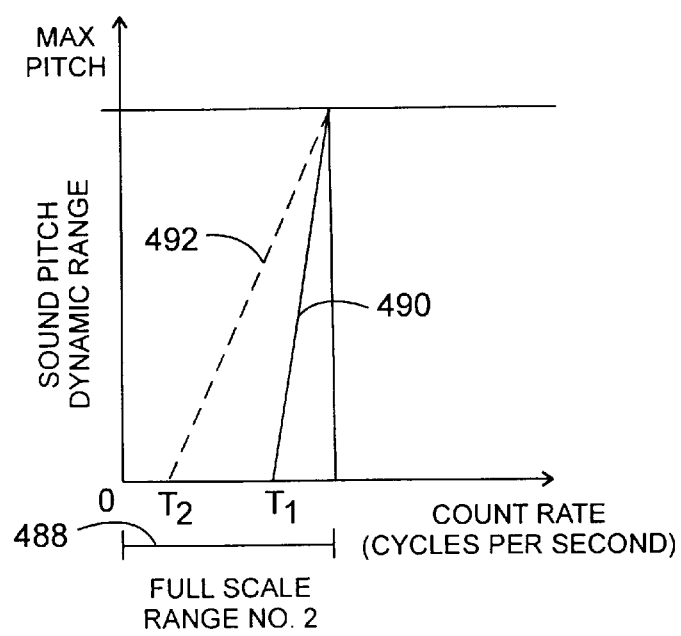

Looking to FIG. 8B, performance for the second range adjustment is represented. In this figure, full scale for the second range is represented at range extent identifier 488. Where the threshold setting is at 70% of full scale, or at T1, then the adjunct system will perform throughout the full dynamic range of available sound pitch as represented by line 490. Correspondingly, for a threshold setting of 20% of full scale as represented at threshold setting $T_2$, full dynamic pitch range will be made available as represented by dashed line 492.

Figure 8C:
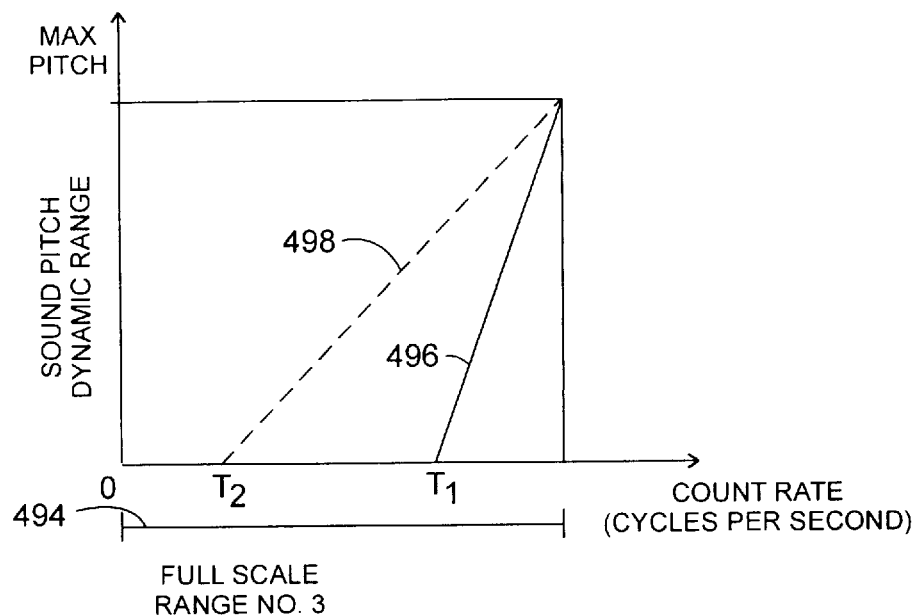

Looking to FIG. 8C, where the third range setting is made, then the full scale in cycles per second of that third range is represented at range delimiter 494. For a threshold setting, $T_1$, of 70%, then the dynamic full scale performance of the system is represented at line 496. Correspondingly, where the threshold is set at $T_2$ or 20% of the count rate full scale, then full scale sound output again is available as represented at dashed line 498.

Figure 8D:
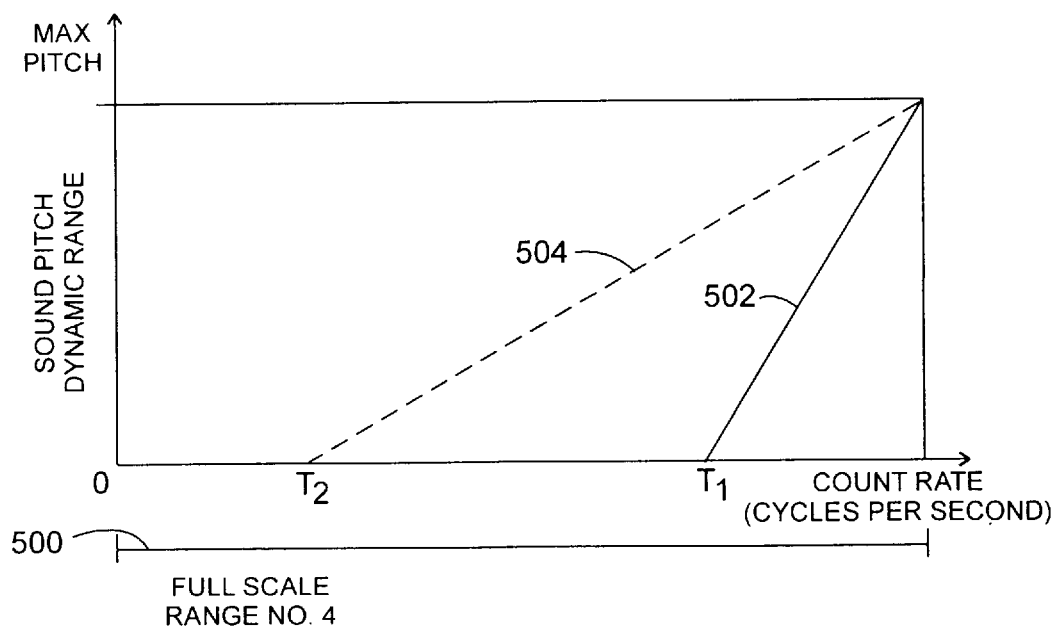

Looking to FIG. 8D, where the fourth setting providing for the largest count rage excursion, then the range delimiter may be represented at 500. Where a threshold of 70% of full scale, i.e. at $T_1$ is elected, then full scale performance will be achieved even at this high threshold position as represented at line 502. Similarly, where a 20% of full scale, $T_2$ is elected, then sound output performance for the entire dynamic range of the system will be developed as represented by dashed line 504.

Figure 9:
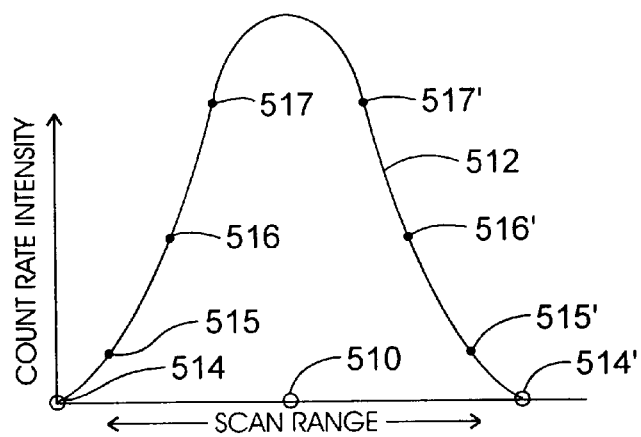
FIG. 9 is a scan range versus count rate intensity curve demonstrating a threshold based guidance technique employed with the system of the invention.

The adjunct system of the invention has particular application to the tracking of lymph ducts and locating a sentinel node. In general, the procedure involves the injection of a radiopharmaceutical at the situs of the neoplastic lesion. The radiopharmaceutical then is permitted to migrate down one or more lymph ducts to a lymph node region. When the radiopharmaceutical is within the duct itself, the attenuation of radiation is with respect to a first power with respect to distance of the crystal within probe 14 from that radiation. As the radiopharmaceutical collects in the first or sentinel lymph node, it becomes what, in effect, may be deemed a point source and second power attenuation occurs over distance from that node. The probe 14 is employed in a scanning technique then over the expected site of the sentinel node. The system of the invention may be used by scanning while increasing threshold values as the crystal at the forward face of the probe 14 moves closer and closer to the node. The availability of full range of pitch output for each threshold setting becomes apparent. Looking to FIG. 9, this scanning arrangement over the sentinel lymph node point source is portrayed graphically. In this figure, count rate intensities during a scan over a regional node basin containing a sentinel node is plotted against the distance the probe is moved in scanning over that region. The sentinel node will be located somewhere within the tissue at the highest point of count rate intensity encountered in a scan. This midpoint is located at 510 in the drawing, and the count rate intensity may be portrayed by the curve 512. With the procedure, an initial range and threshold setting is elected either by adjusting knobs 46 and 48 or by adjusting knob 46 and actuating an up count or down count button 48 or 50 on probe 14. The window of the probe 14 then is positioned at the periphery of the region under investigation, for example, at points 514 or 514'. The probe will be over the sentinel node midway between these points.

Accordingly, the probe is moved inwardly from either of these positions as at 515–515', and the threshold is elevated and/or, a new rate higher dynamic span range is elected. The sound output now is very low in pitch or silent. Note that the range now has narrowed and the probe still be over and pointing down toward the sentinel node when it is over midpoint 510. The surgeon again may move the probe inwardly, for example to location 516 or 516', and again carry out an elevation of threshold. A subsequent scan between those points again is one of narrowed range to bracket the location of midpoint 510 the sentinel node. Threshold elevating procedure again may be carried out by moving the probe inwardly from the last position, for example, to scan between points 517 and 517'. Such a scan will show a very narrow region where the sound output will extend from 0 pitch to essentially maximum pitch. At this juncture, only slight movement of the probe is required to complete a traverse, the location of the sentinel node readily is determined. As noted, the procedure is carried out both in terms of scanning across the scan surface and three-dimensionally through an incision toward the sentinel node.

Figure 10:
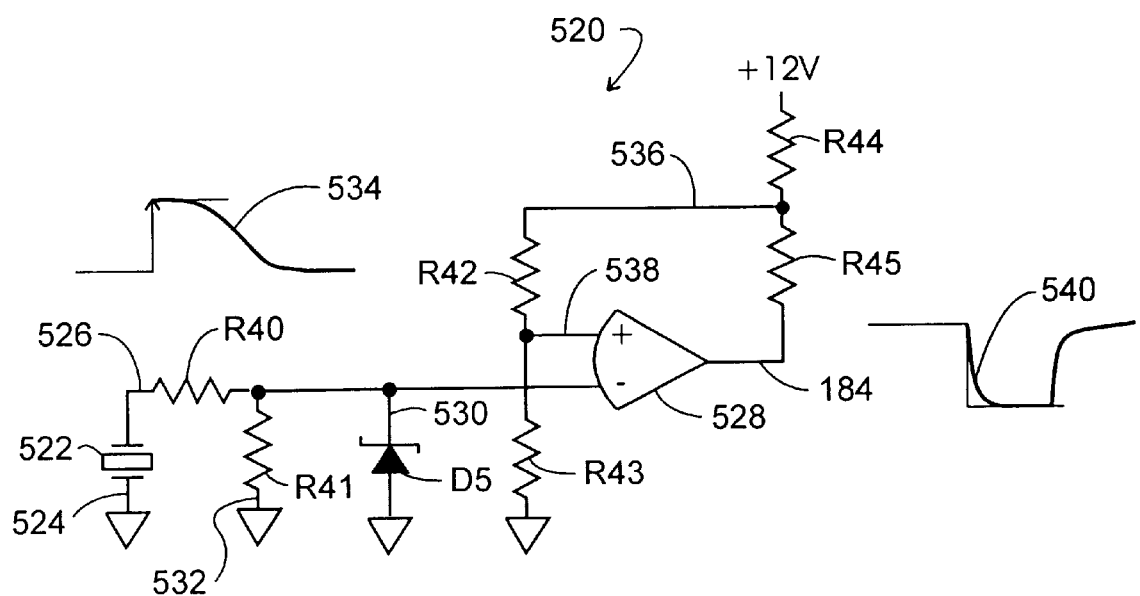
FIG. 10 is an electrical schematic diagram of a circuit employed within the probe shown in FIG. 2 for the purpose of generating current level signals.

Looking to FIG. 10, the circuit by which current level signals may be transmitted along the power supply line of cable 22 from either component of the piezoelectric switch 90 is represented in general at 520. Two such circuits 520 are mounted at printed circuit board 100 described in conjunction with FIGS. 2 and 5A. One such circuit provides a current level in representing an elevation of threshold percentage and a second current level produced by an identical circuit will cause a lowering of the threshold percent value. A piezoelectric component of a switch 90 is represented at 522 having one side coupled to ground via line 524 and the opposite side coupled to line 526 which, in turn, is coupled with the negative terminal of an operational amplifier 528. A resistor R40 is coupled within line 526 in series with piezoelectric device 524 for providing protection against the relatively larger voltage which may be encountered should probe 14 be dropped or otherwise physically shocked. For example, the resistor might have a value of about 100,000 ohms. A Zener diode D5 coupled within a line 530 between line 526 and ground also provides surge protection. A next resistor R41 coupled within line 532 and ground provides a path for d.c. bias current. Resistor R41 also has a relatively larger value, for example, 50 megaohms and develops a time constant with the capacitance associated with device 522 of relatively lengthy value. In this regard, when the piezoelectric switch is actuated, a voltage which may be represented by a curve 534 is generated. The device 522 will generate a voltage, for example, as high as about 6 volts. The output of amplifier device 528 is present at line 184 (see FIG. 5A). Line 184, in turn, is coupled to the +12 v power supply conveyed from the control unit 12 to the probe 14 along relatively lengthy cable 22. Cable 22, for example, may have a length of 12 to 15 feet. Device 528 is configured as a comparator and, accordingly, the positive terminal thereof is coupled to a voltage divider circuit including resistors R42 and R43 coupled within a line 536. The union between these resistors R42 and R43 is tapped at line 538 for connection with the noted positive terminal of device 528. Line 538 extends to line 184 via line 536 at a junction between two resistors R44 and R45 at the output of device 528. The ratio of resistance values for resistors R44 and R45 is, for example, 1:5, and the feedback arrangement is regenerative in order to provide a degree of hysteresis to avoid the spurious results of chattering operations or the like. In general, with the generation of the piezoelectric induced voltage represented at curve 534, a negative going curve will be produced as represented at 540 which will, over a short interval, drop from +12 V to about 0 Volts to produce a pulse of current on the power supply line above the approximately 16 normally required by the preamplification function within probe 14. As noted above,,, a circuit essentially identical to that shown at 520 is employed in conjunction with the second piezoelectric component. In general, circuit 520, as associated with the threshold elevation switching function is arranged to produce about 1.5 milliamperes to represent that actuating signal, while the circuit associated with the down threshold function will generate a pulse of current three or four times greater than that. These pulses or abrupt increases in the current flowing within the 12 V power supply then are detected by the probe switch logic circuit 194 (FIG. 5A). Such a circuit is disclosed in noted application for U.S. patent Ser. No. 08/662,600, now U.S. Pat. No. 5,682,888, (supra).

Since certain changes may be made in the above-described system and apparatus without departing from the scope of the invention herein involved, it is intended that all matter contained in the description thereof or shown in the accompanying drawings shall be interpreted as illustrative and not in a limiting sense.

What is claimed is:

1. A system for detecting and locating a source of photon emissions emanating from tissue within a body, comprising:

a hand manipular probe having a housing, a crystal detector forwardly disposed within said housing responsive to said emissions impinging thereon to provide corresponding detector outputs, and a signal treatment circuit within said housing responsive to said detector outputs to provide count outputs at an output;

a control assembly located remotely from said probe, having an input network for receiving and evaluating said count outputs to derive photon count signals, a converter network responsive to said photon count signals for deriving a rate output level signal corresponding with the frequency of said photon count signals, a threshold network responsive to said rate output level signal to apply a select threshold level value thereto corresponding with a value of the rate of occurrence of said count signals to derive an adjusted count rate signal, a post thresholding amplification network responsive to said adjusted count rate signal and having a gain corresponding with said threshold level value for amplifying said adjusted count rate signal to provide an amplified count rate signal at levels within a predetermined output dynamic range, and an aural cuing network having an aurally perceptive frequency output range corresponding with said predetermined output dynamic range and responsive to said amplified output signal to provide an aurally perceptive cuing output; and transmission means connected with said probe for conveying said count outputs to said control assembly.

2. The system of claim 1 in which:

said converter network derives said rate output level signal as a voltage of given polarity within a dynamic range of voltages extending between minimum and maximum voltage values;

said threshold network includes a summing stage with a summing input for receiving said rate output level signal and a threshold signal corresponding with said threshold level of polarity opposite said given polarity in summing relationship to derive said adjusted rate signal as voltage values within said dynamic range.

3. The system of claim 2 in which said threshold network includes a threshold voltage source and a variable resistor component electrically coupled therewith and manually actuable to provide said threshold signal.

4. The system of claim 1 in which said control assembly threshold network threshold signal is variable to effect derivation of said threshold signal in correspondence with threshold values falling within a predetermined range extending to a maximum threshold value representing a first percentage of said dynamic range.

5. The system of claim 4 in which said first percentage is about 80%.

6. The system of claim 4 in which said predetermined threshold range extends from a minimum threshold value representing a second percentage of said dynamic range less than said first percentage.

7. The system of claim 6 in which said second percentage is about 5%.

8. The system of claim 1 in which:

said threshold network derives said adjusted rate signal as voltage values within a dynamic range of voltage values remaining after application of a threshold voltage value; and said post thresholding amplification network includes an amplification stage and a post threshold variable resistor component coupled in gain defining relationship with said amplification stage.

9. The system of claim 1 in which:

said converter network derives said rate output level signal as a voltage of given polarity within a dynamic range of voltage levels extending between minimum and maximum voltage values;

said threshold network includes a threshold voltage source of polarity opposite said given polarity, a threshold variable resistor component coupled with said source and adjustably actuable to provide a threshold signal corresponding with a selected said threshold level, and a summing stage with a summing input for receiving and summing said rate output level signal and said threshold signal to derive said adjusted rate signal as voltage values remaining subsequent to said summing stage derivation;

said post thresholding amplification network includes an amplification stage and a post threshold variable resistor component coupled in gain defining relationship with said amplification stage and adjustably actuable in correspondence with said threshold variable resistor component actuator to derive said amplified current rate signal.

10. The system of claim 9 in which said threshold variable resistor component and said post threshold variable resistor component are ganged together mechanically actuated potentiometers.

11. The system of claim 9 in which:

said threshold variable resistor component and said post threshold variable resistor component are switch actuated electronic variable resistors having commonly coupled first and second switching inputs, responsive to respectively applied first and second switching conditions to effect a common variable resistor component actuation; and said probe includes first and second probe switches hand actuable to derive respective said first and second switching conditions.

12. The system of claim 1 in which:

said converter network derives said rate output level signal as voltages within a converter dynamic range of voltages; and said control assembly includes a ranging network having a ranging amplification stage with at least two gain orientations selectable in correspondence with predetermined ranges of frequencies of occurrence of said photon count signals and responsive to said rate output level signal at a selected said gain orientation for providing a substantially full scale dynamic range capability for a said rate output level signal derived in correspondence with a said selected gain orientation.

13. The system of claim 1 in which:

said photon count signals are present as pulses exhibiting substantially constant pulse width; and said converter network comprises an R-C integrating stage having a time constant of about one second.

14. The system of claim 1 in which said control assembly includes a dynamic bar graph comprised of a linear array of light emitting devices and a driver circuit responsive to said amplified output signal to energize a number of said light emitting devices corresponding with the amplitude thereof.

15. A system for detecting and locating a source of photon emissions emanating from tissue within a body, comprising:

a hand manipular probe having a housing, a crystal detector forwardly disposed within said housing and responsive to said emissions impinging thereon to provide detector outputs, and a signal treatment circuit responsive to said detector outputs to provide count outputs at an output;

a control assembly having an input network for receiving and evaluating said count outputs to derive photon count signals as pulses exhibiting a substantially constant pulse width, a frequency to voltage converter responsive to said photon count signals for deriving a rate output voltage signal having voltage values within a converter dynamic range of voltages, a ranging network including a ranging amplifier having at least two range designated gain orientations selectable in correspondence with at least two predetermined ranges of rates of occurrence of said photon count signals and responsive to said rate output voltage signal occurring at a selected said gain orientation to provide said rate output voltage signal at substantially full scale range with respect to said converter dynamic range of voltages as a ranged rate output voltage signal of given polarity, a threshold circuit having a summing stage, and a threshold signal network including a threshold variable resistor component actuable to derive a select threshold voltage of polarity opposite said given polarity and corresponding with a threshold percentage of said ranged rate output signal full scale range, said summing stage summing said select threshold voltage and said ranged rate output signal to derive an adjusted count rate signal, an aural cuing network having a frequency output range and responsive to an amplified output signal to generate an aurally perceptive output at a pitch within said frequency output range corresponding therewith, and a post threshold amplification network responsive to said adjusted count rate signal, including an amplification stage and a post threshold variable resistor component coupled in gain defining relationship with said amplification stage and actuable in correspondence with the said actuation of said threshold variable resistor component to derive said amplified output signal at full scale with respect to said frequency output range.

16. The system of claim 15 in which said threshold variable resistor component and said post threshold variable resistor component are ganged together mechanically actuated potentiometers.

17. The system of claim 15 in which:

said threshold variable resistor component and said post threshold variable resistor component are switch actuated electronic variable resistors having commonly coupled first and second switching inputs, responsive to respectively applied first and second switching conditions to effect a common variable resistor component actuation; and said probe includes first and second probe switches hand actuable to derive respective said first and second switching conditions.

18. The system of claim 15 in which said threshold percentage is selectable within a range of percentages extending from a minimum threshold percentage to a maximum threshold percentage.

19. The system of claim 18 in which said minimum threshold percentage is about 5%.

20. The system of claim 18 in which said maximum threshold percentage is about 80%.

21. The system of claim 15 in which said control assembly includes a dynamic bar graph comprised of a linear array of light emitting devices and a driver circuit responsive to said amplified output signal to energize a number of said light emitting devices corresponding with the amplitude thereof.

* * * * *